United States Patent [19]

Vrignaud et al.

[11] Patent Number: 5,177,826
[45] Date of Patent: Jan. 12, 1993

[54] ROTARY TOOTHBRUSH

[75] Inventors: Jean Louis Vrignaud, Paris, France; Albert W. Gebhard, Denver, Colo.; Kenneth J. Hegemann, Carlsbad, Calif.; David W. Roecker, Denver, Colo.

[73] Assignee: Hagemann International, Monaco

[21] Appl. No.: 495,563

[22] Filed: Mar. 16, 1990

[51] Int. Cl.⁵ .................... A61C 17/34; A46B 13/02
[52] U.S. Cl. .......................................... 15/22.1; 15/28
[58] Field of Search ................ 15/22.1, 28, 29

[56] References Cited

U.S. PATENT DOCUMENTS 3,732,589  5/1973  Burki ................................. 15/22.1
4,048,690  9/1977  Wolfson .......................... 15/22.1
4,766,630  8/1988  Hegemann ...................... 15/22.1

Primary Examiner—Edward L. Roberts
Attorney, Agent, or Firm—Darby & Darby

[57] ABSTRACT

A powered toothbrush is provided with a pair of disc-like rotary brushes mounted for rotation about a axis generally perpendicular to the length of the brush. The rotary brushes are in axially spaced relationship and are provided with inwardly directed bristles. Between the rotary brushes, upper and lower linear brushes are mounted above and below the axis of rotation for linear reciprocating motion generally perpendicular to that axis. The upper brush has upwardly directed bristles, and the linear brushes are mounted to the rotary brushes so as to be brought into reciprocal, linear movement when the rotary brushes are reciprocated angularly.

13 Claims, 4 Drawing Sheets

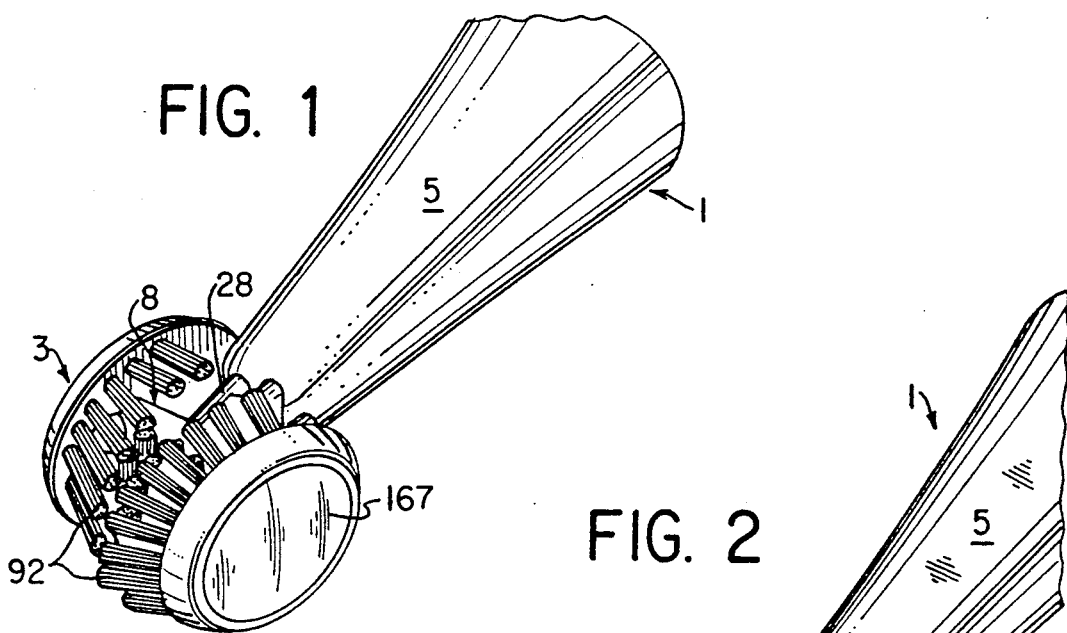
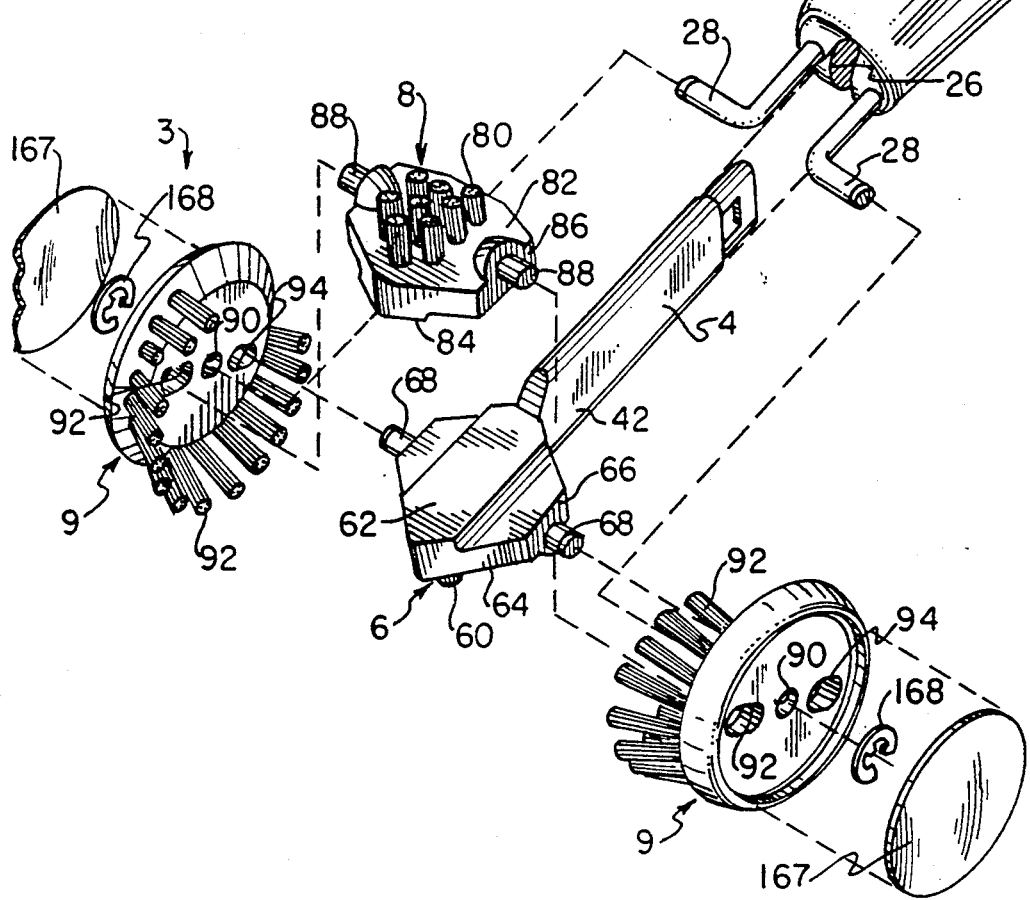

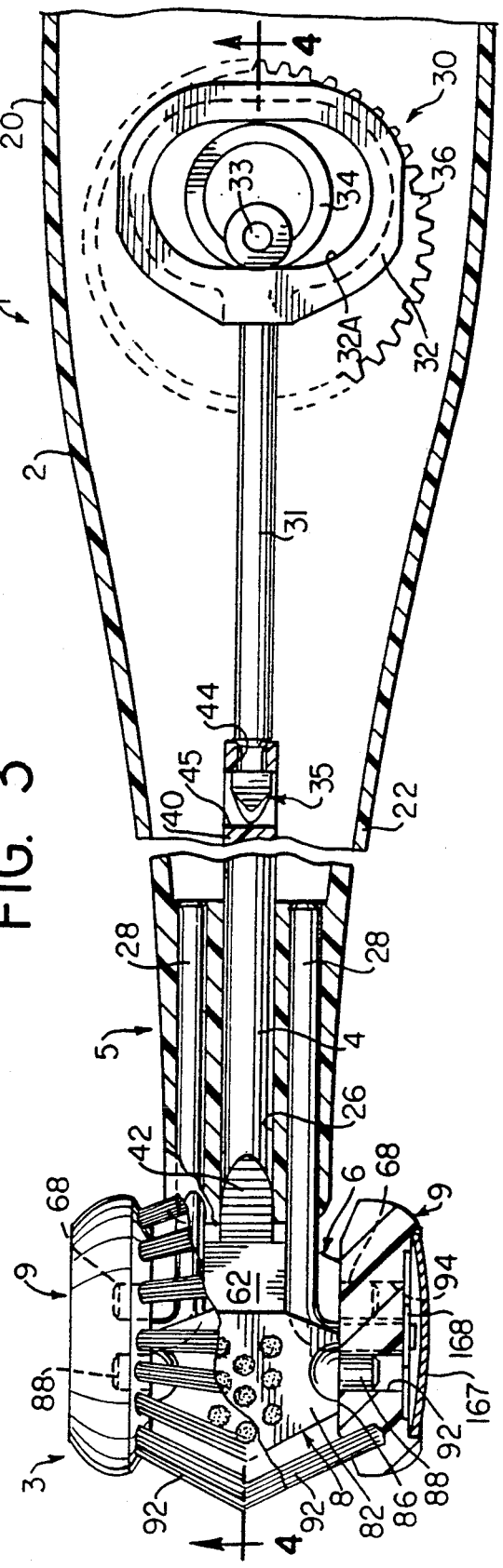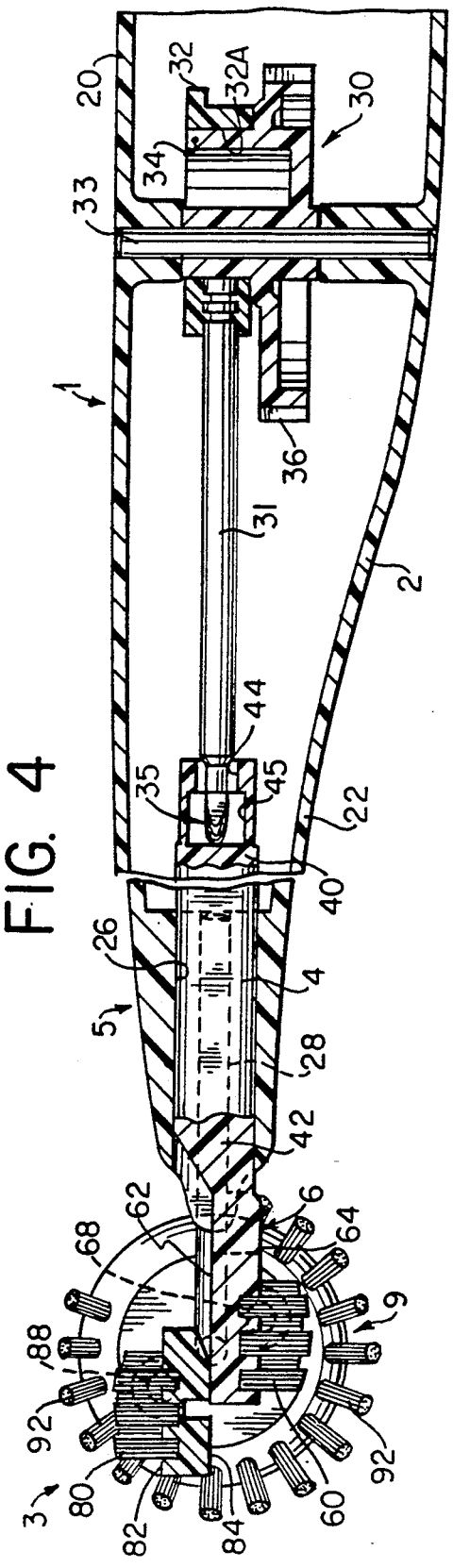

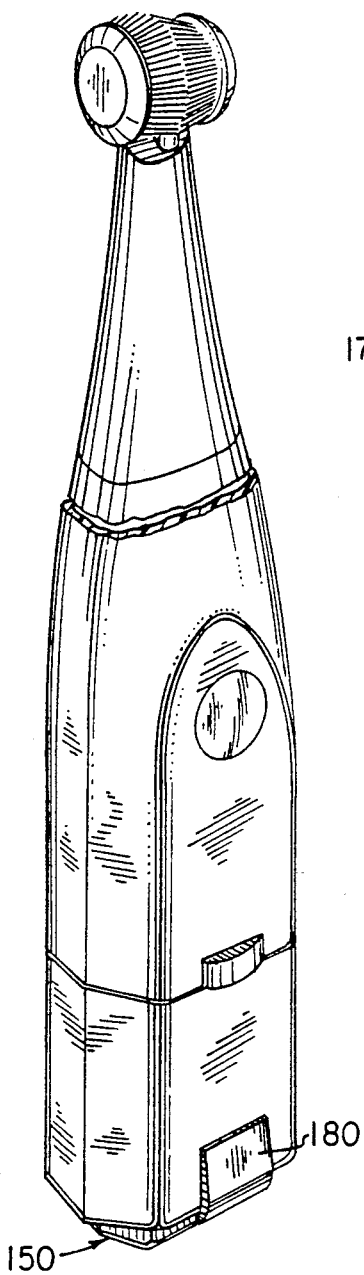
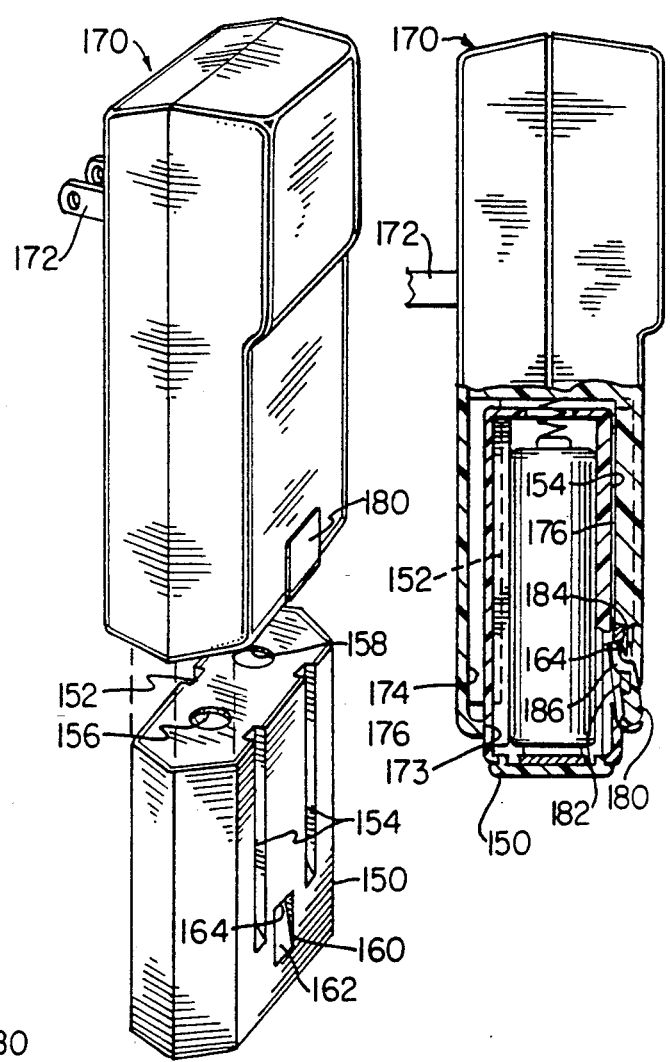
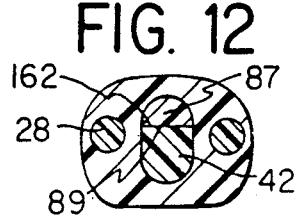
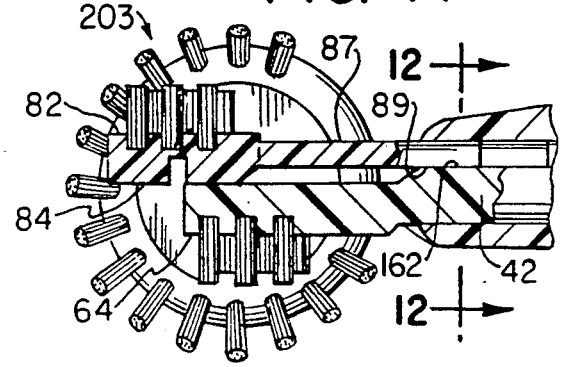

ROTARY TOOTHBRUSH

FIELD OF THE INVENTION

This invention relates generally to a toothbrush and, more particularly, concerns a rotary toothbrush having longitudinally and angularly reciprocating brushes.

BACKGROUND OF THE INVENTION

Power driven toothbrushes are very popular today. The best known type resembles a common manual toothbrush, except that the brush head is vibrated or longitudinally reciprocated against the user's teeth. Although such power brushes simplify brushing of the teeth, to the extent that the amount of manual manipulation of the toothbrush is reduced, the quality of the cleaning of the teeth is not improved, nor is the massaging of the gums.

It has long been recognized that previously unattainable dental cleaning benefits can be achieved with a toothbrush that has twin rotary brushes which straddle the teeth and reciprocate angularly in unison. For example, in U.S. Pat. No. 4,048,690, issued to Wolfson on Sep. 20, 1977, a toothbrush is disclosed which includes such rotary brushes, as well as an upwardly directed and a downwardly directed stationary brush between the rotary brushes. This toothbrush has the advantage of being able to clean both surfaces of both rows of teeth and the biting edges simultaneously. Since the toothbrush is powered, rotary brushes are particularly effective at abradably removing plaque and sweeping it away. However, the stationary brushes, which clean the biting surfaces of the teeth can be utilized only by moving the entire toothbrush and, in this sense, the toothbrush is no better than a manual toothbrush. Also, the construction of this toothbrush proved to be too large and bulky to fit and operationally function within the mouths of persons have average or small mandibles.

U.S. Pat. No. 3,732,589, issued to Burki on May 15, 1973 discloses a powered rotary toothbrush in which radially directed bristles are provided between twin rotary brushes. Although this results in a reduced size and produces some power cleaning of the biting surfaces of the teeth, the rotary action of the radially directed bristles is not particularly effective in cleaning the biting surfaces of the teeth. Manual movement of the toothbrush is still necessary.

U.S. Pat. No. 4,766,630, issued to Hegemann on Aug. 30, 1988 discloses a powered toothbrush which includes a pair of longitudinally extending, reciprocal stroke arms extending between the rotary brushes and disposed above and below their axis of rotation, respectively. The stroke arms are secured, by axially directed pins between the rotary brushes, and the portion of the upper arm between the rotary brushes includes upwardly directed bristles, while the portion of the lower stroke arm includes downwardly directed bristles. When the stroke arms are oppositely reciprocated, reciprocated, annular movement of the rotary brushes is achieved. At the same time, the bristles on the stroke arm achieve reciprocal linear movement. For the first time, it was possible to achieve effective power cleaning of both surfaces and the biting edges of both rows of teeth simultaneously. However, the need to use the dual reciprocal arms made the body of the brush too bulky and interfered with convenient use of the brush.

The need exists for a toothbrush which has both longitudinally and rotary reciprocating brushes to effectively clean the teeth and gums, but which is composed of relatively few components and is sufficiently small so that even users with smaller mandibles and mouths can use it without discomfort.

In accordance with a preferred embodiment of the present invention, a powered toothbrush is provided with a pair of disc-like rotary brushes mounted for rotation about a axis generally perpendicular to the length of the brush. The rotary brushes are in axially spaced relationship and are provided with inwardly directed bristles. Between the rotary brushes, upper and lower linear brushes are mounted above and below the axis of rotation for linear reciprocating motion generally perpendicular to that axis. The upper brush has upwardly directed bristles, and the lower brush has downwardly directed bristles, and the linear brushes are mounted to the rotary brushes so as to be brought into reciprocal, linear movement when the rotary brushes are reciprocated angularly. Reciprocal motion can then be applied to one of the linear brushes or to the rotary brushes, in order to bring the entire mechanism into reciprocal motion.

BRIEF DESCRIPTION OF THE DRAWINGS

The foregoing brief description, as well as further objects, features and advantages of the present invention will be understood more completely from the following detailed description of presently preferred embodiments in accordance with the present invention, with reference being had to the accompanying drawings, wherein:

FIG. 1 is a fragmentary perspective showing the forward portion of a rotary toothbrush embodying the present invention in an assembled position;

FIG. 2 is an exploded perspective view corresponding to FIG. 1 and showing the components of the rotary toothbrush, with parts shown;

FIG. 3 is a bottom plan view with respect to FIG. 1 showing a more extensive portion of the rotary toothbrush, with parts shown in section, to illustrate internal structural details;

FIG. 4 is a fragmentary sectional view, taken along lines 4—4 of FIG. 3 showing the front portion of the rotary toothbrush-in an assembled position;

FIG. 10 is a perspective view of a preferred embodiment of the entire toothbrush 1 shown assembled and including a rechargeable battery pack;

FIG. 11 is a sectional view, similar to the left hand portion of FIG. 4, illustrating an alternate embodiment of the brush head assembly;

FIG. 12 is a sectional view taken along line 11—11 in FIG. 11 looking towards the rear of the toothbrush;

FIG. 13 is an exploded view of the battery charger and the battery pack utilized in toothbrush 1; and FIG. 14 is a right-side view with respect to FIG. 13, with the bottom portion shown in section, to illustrate the structural details of the battery charger and the battery pack.

DETAILED DESCRIPTION OF THE PREFERRED EMBODIMENT

Figure 5:
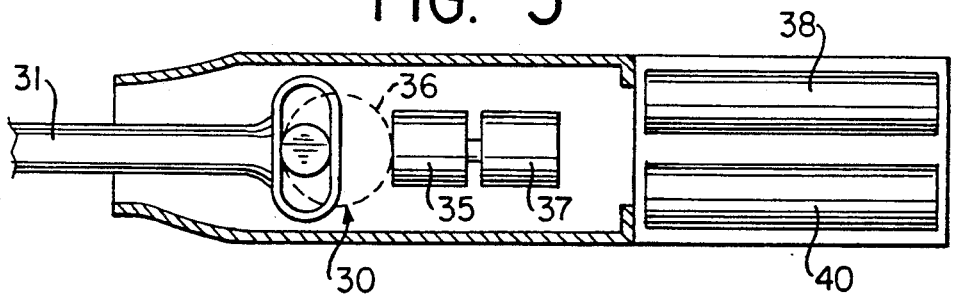
FIG. 5 is a fragmentary schematic sectional view, corresponding to FIG. 4, but showing the rear portion of the toothbrush on a reduced scale, and, in particular, showing its driving mechanism.

Referring now to the drawings wherein like reference numerals represent identical or corresponding parts throughout the several views, FIGS. 1 and 2 are fragmentary assembled and exploded views, respectively, of a rotary toothbrush 1 embodying the presently preferred form of the invention. Toothbrush 1 broadly comprises a brush head assembly 3, a housing 5, and a longitudinal driving arm 4 which is received in housing 5 and provides for movement of brush head assembly 3.

Brush head assembly 3 comprises a lower brush 6 disposed at the front end of longitudinal arm 4, an upper brush head 8 disposed above lower brush 6, and a pair of rotary brushes 9 mounted on opposite sides of lower and upper brushes 6, 8 for rotation about an axis which is transverse relative to arm 4. The structure and interaction of these components is described in more detail below.

Lower brush 6 has a top surface 62, a bottom surface 64 and side surfaces 66. A pair of shafts 68 extend outwardly from respective opposite side surfaces 66, and a plurality of bristles 60 (FIG. 4) extend perpendicularly downwardly from bottom surface 64. The bristles 60 are secured by conventional means, such as being received in holes formed in bottom surface 64.

Upper brush 8, is preferably the same size as lower brush 6 and has a top surface 82, a bottom surface 84 (see FIG. 4) and side surfaces 86. A pair of shafts 88 extend outwardly from respective opposite side surfaces 86 of upper brush 8. A plurality of bristles 80, are preferably secured in holes formed in top surface 82, so as to extend perpendicularly upwardly from top surface 82 so that the bristles 80 of upper brush 8 and bristles 60 of lower brush 6 extend in opposite directions when the toothbrush is assembled, as shown in FIG. 4.

A rotary brush 9, disc-like in configuration, is disposed on either side of the brushes 6 and 8. Each rotary brush 9 has a plurality of circumferentially spaced bristles 92 facing inwardly towards upper and lower brushes 8, 6. Bristles 92 are advantageously angled slightly radially outwardly in a direction away from the central axis of rotary brush 9 so that bristles 92 spread apart as they project upwardly.

A central portion of each rotary brush 9 includes three apertures having parallel axes: a central aperture 90, an upper aperture 92 and a lower aperture 94. The upper and lower apertures receive the shafts of upper and lower brushes 6 and, 8 respectively, and are preferably oblong, as will be explained further below.

Rotary brushes 9 are mounted on shafts 28 for rotation relative to housing 5 (discussed further below) with each shaft 88 of upper brush 8 extending within an upper aperture 94 and each shaft 68 of lower brush 6 is extending within a lower aperture 92. A wheel cap 167 is press-fitted within a circular recess formed in the outer surface of rotary brush 9 and conceals a snap-ring-like clip 168, which is mounted on and captures shaft 28 after it is passed through central aperture 90. When the brush head assembly 3 is assembled, upper brush 8 lies atop lower brush 6 so that bottom surface 84 of upper brush 6 and the top surface 62 of lower brush 6 are in abutment or close opposition, and shafts 88 are above shafts 68:

Lower brush 6 is mounted at the front end 42 of longitudinal arm 4 and is preferably integral therewith. Arm 4 is shaped so as to be substantially taller than it is wide, so that it projects substantially above the upper surface of brush 6. Brush 8 then fits into the "space" formed in the front of this upwardly projecting portion of arm 4. This results in a particularly compact construction, in which the reciprocating brushes 6, 8, hardly occupy more of vertical space then the arm 4 itself (see e.g. FIG. 4). The brush assembly therefore occupies minimum height, and this increases the comfort of the user of a toothbrush, particularly a user with a small mouth.

Figure 7:
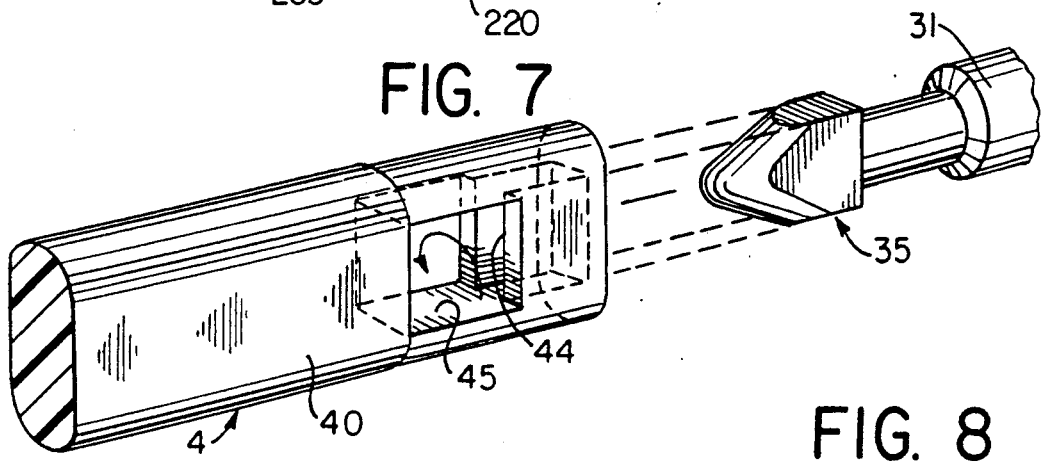
FIG. 7 is an enlarged, fragmentary, perspective view showing structural details at the rear of longitudinal arm 4.

As best seen in FIG. 7, a tall, narrow passageway 44 is provided at the rear end 40 of arm 4 and extends forwardly within the arm. It is intersected by a passageway 45 which extends laterally through the arm at a position forward of the rear end 40. As will be described in further detail below, these passageways form part of a connecting arrangement which couples the rear end of arm 4 to a drive shaft of a driving mechanism, providing front-to-rear reciprocal motion to arm 4.

Turning now to the housing assembly 5, and in particular to FIGS. 1 and 3, housing assembly 5 includes a main body 2 and a driving mechanism 30 disposed within body 2. Body 2 is hollow and generally conically shaped. It tapers from a rear portion 20 to a front portion 22 so that its diameter in the rear is greater than its diameter in front. A front opening 26 is formed in the front portion 22, through which the longitudinal arm 4 is received in body 2, to connect with driving mechanism 30.

A pair of rigid, spaced apart, generally L-shaped supporting elements 28, project forwardly from body 2 on either side of opening 26. Each element 28 extends laterally outwardly in a direction away from longitudinal arm 4, to form an axle which is received in central aperture 90 of one of rotary brushes 9.

In the preferred embodiment, the body 2 is formed in two separate parts. The front part includes the supporting elements 28, 28, and the rear part includes the driving mechanism 30. These two parts are secured together by means of a bayonet-type connection (not shown), which permits the two parts of the body to be connected or disconnected by effecting a 90° relative rotation between the two parts. Since the front part of the body contains the brush assembly and the longitudinal arm 4, it is preferable to form the brush assembly, supporting elements 28 and the longitudinal arm 4 as a unit together with the front part of body 2. This unit is then readily removed and replaced as the various brushes wear out and need replacement.

The drive assembly 30 includes a drive shaft 31, which has an arrowhead-shaped tip 35 at its forward end. The tip 35 is relatively thin in its dimension perpendicular to the plane of FIG. 3. This thin dimension of tip 35 and its height are such that the tip will be received within passageway 44 formed at the rear end of arm 4 and,, as arm 4 shaft 31 are brought together, head 35 passes forwardly (indicated by the arrow in FIG. 7), beyond passageway 44 and into passageway 45. Subsequently, a 90° relative rotation is provided between the forward and rear portions of housing 2, in order to secure them together by means of a conventional bayonet-type connection (not shown). This causes head 35 to rotate 90° within passageway 45, whereby it is brought into the position shown in FIGS. 3 and 4. In this position, tip 35 is captured within passage 45, since it is substantially taller then the width of passageway 44 and cannot be withdrawn therethrough.

At the rear of shaft 31, there is provided a yoke member 32 which includes an interior, oblong bearing surface 32a. A cylindrical cam element 34 is disposed within bearing 32 and is mounted for eccentric rotation about an axle 33 fixed within housing 5. Secured to cam element 34, but mounted for concentric rotation about axle 33 is a gear 36. In operation, when gear 36 is driven into rotation, cam element 34 is driven into eccentric rotary motion about axle 33. Since cam 34 is captured within yoke 32, shaft 31 is driven into linear, front-to-rear reciprocal motion. This, in turn, drives arm 4, which causes brush 6 to move linearly, whereby brushes 9 are driven into angular reciprocal motion. The motion of brushes 9, in turn, causes brush 8 to move linearly.

FIG. 5 is a schematic representation showing the rear portion of the drive assembly 30. In addition to the components already discussed, the toothbrush includes batteries 38 and 39 to provide electrical power, an electric motor 37 powered by the batteries, and a mechanical linkage 35 between motor 37 and gear 36. The mechanical linkage could simply be an arrangement of gears connecting gear 36 to the output shaft of motor 37.

Figure 6:
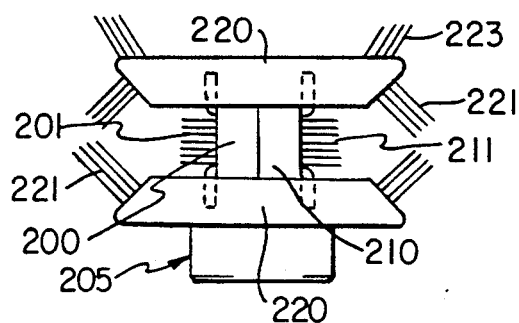
FIG. 6 illustrates an alternate embodiment of the brush configuration of the rotary toothbrush.

FIG. 6 illustrates an alternate embodiment 200 of a rotary toothbrush in accordance with the present invention. In this case, the rotary brushes 220 are mounted for rotation about a common axis and are driven into rotary motion in the same manner as disclosed in U.S. Pat. No. 3,732,589. The brush heads 205 and 210 are similar to brush head 8 of FIGS. 2-4 and are mounted to the rotary brushes 220 in the same manner. Accordingly, when the lower rotary brush 220 is driven into rotation, the brushes 205 and 210 are driven into linear, reciprocal motion perpendicular to the plane of FIG. 6. This causes the upper rotary brush 220 to be driven into rotary motion. The rotary brushes 220 are provided with bristles 221, which correspond to the bristles 92 of brushes 9, and the brushes 205 and 210 are provided with bristles 201 and 211, respectively, which correspond to the bristles 80 of brush head 8. In addition, upper rotary brush head 222 is provided with outwardly directed bristles 223, to provide for more convenient polishing of the front of the teeth.

Figure 8:
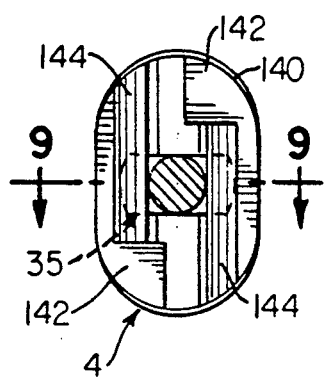
FIG. 8 is a rear view of an alternate embodiment 140 of the rear portion 40 of longitudinal shaft 4.
Figure 9:
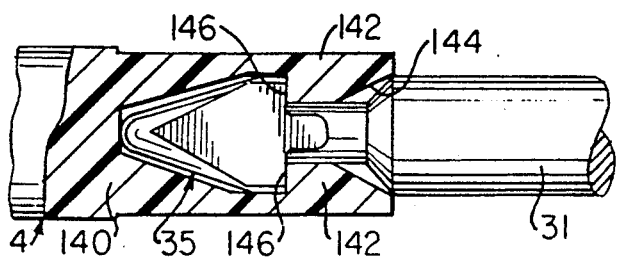
FIG. 9 is a sectional view taken along line 9—9 in FIG. 8 and looking in the direction of the arrows, showing shaft 31 inserted within longitudinal arm 4 to illustrate their interaction.

FIGS. 8 and 9 illustrate an alternate embodiment 140 of the rear end 40 of arm 4. FIG. 9 should be compared to FIG. 3, which shows the arm 4 in a similar, cut-away view. In the rear portion 140, the arrowhead-shaped tip 35 is received in a passageway defined between two spaced arms 142. Each of these arms includes a forwardly and radially inwardly tapering ramped face 144, which terminates in substantially vertical (in FIG. 9) face 146. In use, if the head 35 were inserted in the rear of arm 4, between arms 142, while in the orientation shown in FIG. 8, the shape of the head and the ramped surfaces 144 would cause the arms 142 to spread due to their resilience, as head 35 is urged forward. When head 35 clears the surfaces 146, the arms 142 snap back towards each other, owing to their resilience, capturing head 35 as shown in FIG. 8. As a result of this construction, it is not necessary to bring arm 4 to its rearmost position prior to assembling the toothbrush head to the main body. If such assembly takes place with the arm 4 in its forward position, when shaft 31 begins reciprocating, it will be forced into the rear of arm 4, and the connection will be made as explained above.

As best seen in FIG. 8, ramp surfaces 144 do not extend for the full height of the arms 142. Instead, diagonally opposite corners 146 of the arms are left intact. This is beneficial, because rear portion 140 is relatively small and would tend to be too flexible or too weak if there were full height ramped surfaces 144.

FIG. 10 is an assembled view of a preferred embodiment of the entire toothbrush 1, intended to illustrate the rechargeable battery feature of the present invention. Rechargeable batteries are stored in a battery pack or housing 150 (discussed in further detail below), which is slidably received in the bottom of the toothbrush. Battery housing 150 may be removed from the toothbrush by operating a spring loaded latch or locking mechanism 180, to release it.

The battery pack or housing 150 is illustrated in greater detail in FIGS. 13 and 14, in conjunction with a battery charger 170. Battery charger 170 is provided with a conventional electrical plug 172, so that it may be plugged directly into an outlet for house circuit. The battery charger 170 is provided with an open bottom 173 and is made hollow to include a receiving compartment 174 for the battery pack 150, which is inserted through the open bottom 173.

Battery pack 150 includes a single upright groove 152 on one surface and a pair of upright grooves 154 on the opposite surface. These grooves slidably receive ribs 176 on the interior of compartment 174 of charger 170. This assures that the battery pack 150 can be received within charger 170 in only one orientation, whereby the terminals 156, 158 of the battery pack 150 are always in a correct electrical orientation.

Battery pack 150 also includes a rectangular recess 160. Within recess 160, a ramp surface 162 slopes upwardly and inwardly into the battery pack. Surface 162 terminates at an upper edge wall 164 of recess 160. Wall 164 is generally perpendicular to the outer surface of the battery pack. Just above the opening 173, charger 170 includes a locking mechanism 180, which is pivotally mounted at 182 and loaded by a spring 184, which urges the rear end 186 of locking mechanism 180 towards the interior of the battery compartment in charger 170. When battery pack 150 is inserted into storage compartment 174 of charger 170 and moved upward, spring 184 will urge rear end 186 into recess 160 as soon as wall 164 passes end 186. This causes the battery pack 150 to be locked within the compartment 174, so that its terminals 156 and 158 are in electrical contact with mating terminals within charger 170. If charger 170 is plugged into an electrical outlet, batter pack 150 will then be charged. Those skilled in the art will appreciate that the upper portion of charger 170 must include conventional circuitry to convert alternating current power to a direct current voltage necessary to charge the battery pack 150. Battery pack 150 may be removed from charger 170 by pressing the bottom of locking mechanism 180 inward until its end 186 is withdrawn from recess 160 within the battery pack 150. The battery pack will then drop downwardly, out of compartment 174.

Those skilled in the art will appreciate that the bottom of toothbrush 1 must be constructed in the same manner as the bottom of charger 170. This permits insertion, retention and removal of battery pack 150 in the same manner as described with respect to battery charger 170.

FIGS. 11 and 12 illustrate an alternate embodiment 203 of brush head assembly 3. In this embodiment, corresponding elements have been numbered with the same reference characters as appear in FIG. 4. The essential difference in brush head assembly 203 lies in the construction of the upper brush 8. As previously explained, the brush 8 is constructed to fit and slide within the "space" formed at the front 42 of arm 4. In brush head assembly 203, upper brush 8 includes a semi-cylindrical, rearwardly projecting shaft 87, the flat surface 89 of which is in sliding contact with surface 162 of arm 4. Shaft 87 is received in front opening 26 of toothbrush body 20, along with longitudinal arm 4. This assures that flat surface 89 will remain in intimate sliding contact with surface 162. The overall effect of providing shaft 87 is to assure that brush 8 experiences only linear motion and does not pivot about an axis passing through the shafts 88, 88'.

Although preferred embodiments of the invention have been disclosed for illustrative purposes, it will be appreciated by those skilled in the art that many additions, modifications, and substitutions are possible without departing from the scope and spirit of the invention as defined in the accompanying claims. For example, a somewhat less effective, but nonetheless useful, toothbrush would be obtained if only one rotary brush were used. It would still be possible to utilize two linear brushes.

What is claimed is:

1. A toothbrush comprising;
a elongated main body;
a generally disc-shaped rotary brush having generally axially directed peripheral bristles;
axle means mounting said rotary brush to said main body for rotational movement about an axis which is transverse to the length of said body;
means at least partially disposed in said main body for providing reciprocating, rotary motion to said rotary brush;
a linear brush having bristles directed away from said axis; and
means for mounting said linear brush to said rotary brush so that said linear brush reciprocates linearly along the length of said body as said rotary brush reciprocates rotationally.

2. A toothbrush in accordance with claim 1, further comprising a second linear brush having bristles directed away from said axis and oppositely to the bristles of the other linear brush, and means for mounting said second linear brush to said rotary brush so that said linear brush reciprocates linearly along the length of said body as said rotary brush reciprocates rotationally.

3. A toothbrush in accordance with claim 2, wherein said means for providing comprises a longitudinal arm mounted for reciprocal movement along the length of said body, said arm being connected at a first end to one of said linear brushes, said arm imparting linear motion to said one linear brush, the means for mounting said linear brush producing reciprocating rotary motion of the rotary brush.

4. A toothbrush in accordance with claim 3 further comprising a guide arm projecting from the other of said linear brushes and means for retaining said guide arm in a fixed orientation for sliding movement relative to said longitudinal arm.

5. A toothbrush in accordance with claim 2, further comprising a second generally disc-shaped rotary brush having peripheral bristles generally axially directed towards the other rotary brush;
second axle means mounting said second rotary brush for rotational movement about said axis;
said linear brush being also mounted to said second rotary brush so as to be reciprocated linearly when said rotary brushes experiences reciprocating rotary motion.

6. A toothbrush in accordance with claim 5, wherein said means for providing comprises a longitudinal arm mounted for reciprocal movement along the length of said body, said arm being connected at a first end to one of said linear brushes, said arm imparting linear motion to said one linear brush, the means for mounting said linear brush producing reciprocating rotary motion of the rotary brushes.

7. A toothbrush in accordance with claim 6, wherein said longitudinal arm is coupled at a second end to a linearly reciprocating drive shaft, said longitudinal arm having a tall, narrow width passageway extending thereinto from said second end and a laterally directed passageway extending therethrough at a distance away from said second end, a drive shaft having a forward portion dimensioned and shaped to be received in said tall, narrow passageway and to be substantially larger in height than the width of said passageway, said forward portion, terminating at a short distance rearward of said drive shaft, whereby said drive shaft may be inserted into said tall, narrow passageway and moved forward into said lateral passageway, wherein relative rotation between said longitudinal arm and said drive shaft causes said forward portion of said drive shaft to extend into said lateral passageway and to be captured therein.

8. A toothbrush in accordance with claim 1, further comprising a second generally disc-shaped rotary brush having peripheral bristles generally axially directed towards the other rotary brush;
second axle means mounting said second rotary brush for rotational movement about said axis; and
means for mounting said linear brush to said second rotary brush so that said linear brush reciprocates linearly along the length of said body as said second rotary brush reciprocates rotationally.

9. A toothbrush in accordance with claim 8, wherein said means for providing comprises a longitudinal arm mounted for reciprocal movement along the length of said body, said arm being connected at a first end to said linear brush, said arm imparting linear motion to said one linear brush, the means for mounting said linear brush producing reciprocating rotary motion of the rotary brushes.

10. A toothbrush in accordance with claim 1, wherein said means for providing comprises a longitudinal arm mounted for reciprocal movement along the length of said body, said arm being connected at a first end to said linear brush said arm imparting linear motion to said linear brush, the means for mounting producing reciprocating rotary motion to the rotary brush.

11. A toothbrush in accordance with claim 10, wherein said longitudinal arm is coupled at a second end to a linearly reciprocating drive shaft, said longitudinal arm having a tall, narrow width passageway extending thereinto from said second end and a laterally directed passageway extending therethrough at a distance away from said second end, a drive shaft having a forward portion dimensioned and shaped to be received in said tall, narrow passageway and to be substantially larger in height than the width of said passageway, said forward portion, terminating at a short distance rearward of said drive shaft, whereby said drive shaft may be inserted into said tall, narrow passageway and moved forward into said lateral passageway, wherein relative rotation between said longitudinal arm and said drive shaft causes said forward portion of said drive shaft to extend into said lateral passageway and to be captured therein.

12. A toothbrush in accordance with claim 10, wherein said longitudinal arm is coupled at a second end to a linearly reciprocating drive shaft, said longitudinal arm having a pair of opposed arms projecting beyond its second end as an extension thereof, each opposed arm having a sloped surface facing the other opposed arm to form a gap between said opposed arms which tapers towards said second end, a drive shaft having a tapered end conforming generally in taper to the gap between said opposed arms, the tapered end of said drive shaft being too large to fit through said gap, the opposed arms separating to admit said tapered end when it is urged into said gap.

13. A toothbrush in accordance with claim 1 further comprising means defining a compartment in said toothbrush, a battery pack dimensioned and shaped to be slidably received in said compartment and means for releasably retaining said battery pack in said compartment.

* * * * *